(12) United States Patent
Gilmore et al.

(10) Patent No.: US 8,971,983 B2
(45) Date of Patent: Mar. 3, 2015

(54) DISPOSABLE LOW-PROFILE CONFORMABLE BIOMEDICAL SENSOR

(71) Applicant: Altec, Inc., Boston, MA (US)

(72) Inventors: L. Donald Gilmore, Wellesley, MA (US); Carlo J. De Luca, Wellesley, MA (US)

(73) Assignee: Altec, Inc., Boston, MA (US)

( * ) Notice: Subject to any disclaimer, the term of this patent is extended or adjusted under 35 U.S.C. 154(b) by 157 days.

(21) Appl. No.: 13/856,009

(22) Filed: Apr. 3, 2013

(65) Prior Publication Data

US 2013/0261422 A1    Oct. 3, 2013

Related U.S. Application Data

(60) Provisional application No. 61/619,596, filed on Apr. 3, 2012.

(51) Int. Cl.
*A61B 5/0492*    (2006.01)

(52) U.S. Cl.
CPC .......... *A61B 5/0492* (2013.01); *A61B 2562/043* (2013.01); *A61B 2562/046* (2013.01); *A61B 2562/222* (2013.01)
USPC ............................ 600/391; 600/392; 600/393

(58) Field of Classification Search
CPC ........... A61B 5/0492; A61B 2562/043; A61B 2562/182
USPC .................................................. 600/391–393
See application file for complete search history.

(56) References Cited

U.S. PATENT DOCUMENTS

| | | | |
|---|---|---|---|
| 4,763,660 A * | 8/1988 | Kroll et al. ..................... | 600/391 |
| 5,125,405 A | 6/1992 | Schmid | |
| 6,047,202 A | 4/2000 | Finneran et al. | |
| 6,238,338 B1 | 5/2001 | DeLuca et al. | |
| 6,440,067 B1 | 8/2002 | DeLuca et al. | |
| 6,480,731 B1 | 11/2002 | DeLuca et al. | |
| 6,597,944 B1 | 7/2003 | Hadas | |
| 6,654,626 B2 * | 11/2003 | Devlin et al. .................. | 600/383 |
| 6,687,524 B1 | 2/2004 | Svejk | |
| 6,950,688 B2 | 9/2005 | Axelgaard et al. | |
| 7,627,358 B2 | 12/2009 | Finneran et al. | |
| 7,697,999 B2 | 4/2010 | Axelgaard | |
| 7,941,202 B2 * | 5/2011 | Hetke et al. ................... | 600/377 |
| 7,957,785 B2 | 6/2011 | Nishimura | |
| 8,019,402 B1 | 9/2011 | Kryzpow et al. | |
| 8,032,210 B2 | 10/2011 | Finneran et al. | |
| 8,311,603 B2 * | 11/2012 | Faersnes et al. .............. | 600/372 |

(Continued)

FOREIGN PATENT DOCUMENTS

WO    WO 2007/095457    8/2007

*Primary Examiner* — Lee S Cohen
(74) *Attorney, Agent, or Firm* — Muirhead and Saturnelli, LLC

(57) ABSTRACT

A disposable, low profile biomedical sensor for detecting electrical signals from muscles and which consists of a framework of malleable and flexible component layers supporting an arrangement of conductor leads embedded within electrically conductive, adhesive, cross-linked hydrophilic polymer gel components configured to form signal detection and reference electrode contacts. The combination of component layers provides a sensor and lead cable that is flexible and can be contoured to conform to the underlying musculature. The mechanical and electrical configurations act in synergy to shield the sensor and lead cable from external electrical fields and suppress movement artifact.

22 Claims, 11 Drawing Sheets

(56) References Cited

U.S. PATENT DOCUMENTS

| | | |
|---|---|---|
| 2005/0096513 A1 | 5/2005 | Ozguz et al. |
| 2006/0079801 A1 | 4/2006 | DeLuca et al. |
| 2009/0036792 A1 | 2/2009 | DeLuca et al. |
| 2010/0261992 A1 | 10/2010 | Axelgaard |
| 2011/0028823 A1 | 2/2011 | Gilmore et al. |
| 2011/0077497 A1 | 3/2011 | Oster et al. |
| 2011/0190615 A1* | 8/2011 | Phillips et al. ............... 600/372 |

* cited by examiner

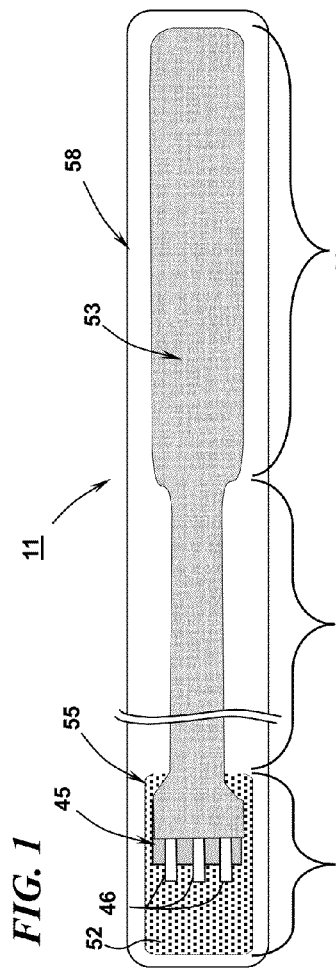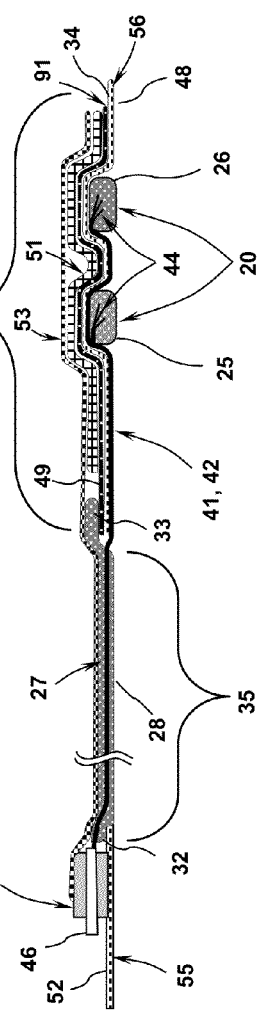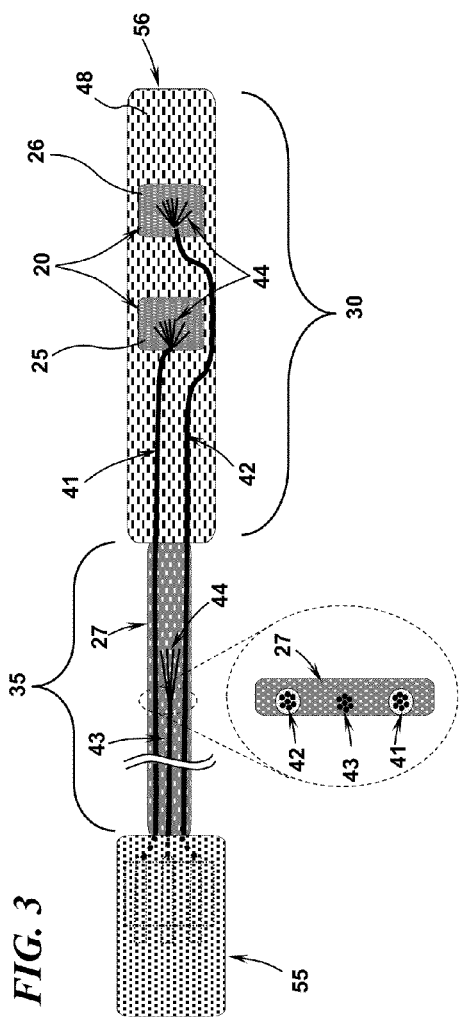

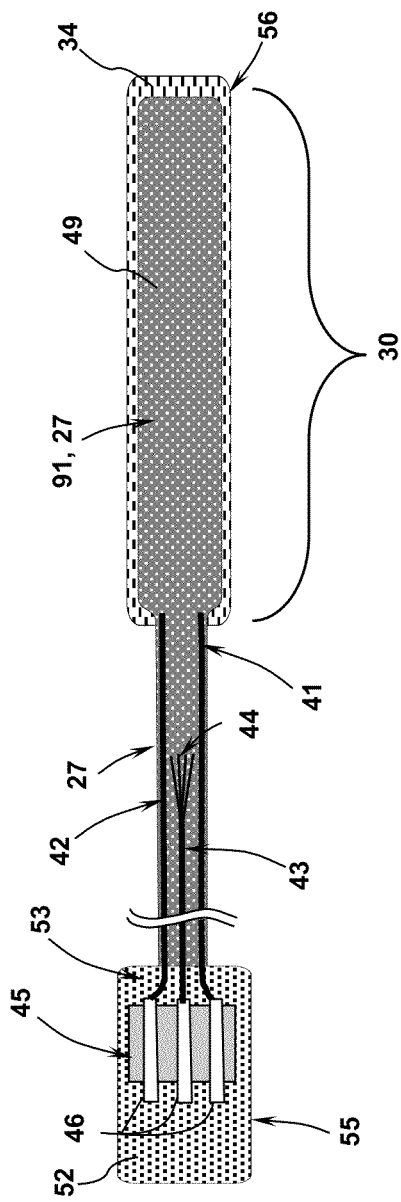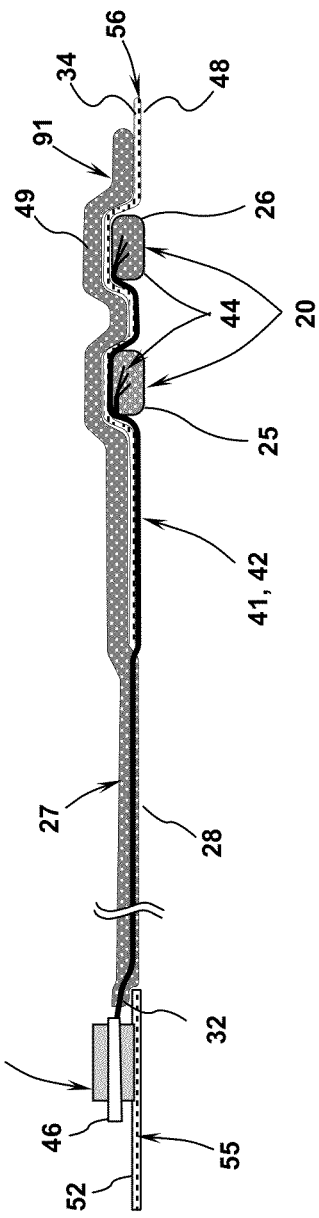
FIG. 7A
FIG. 7B

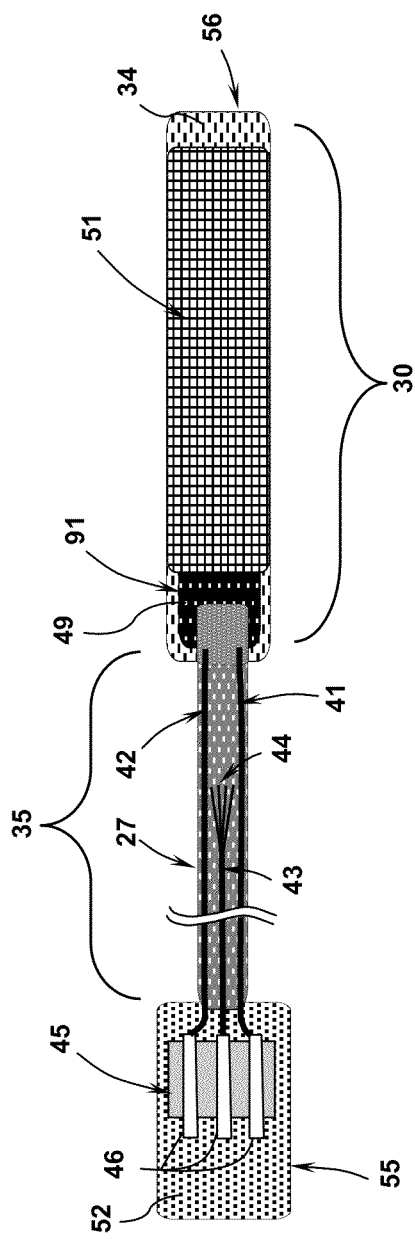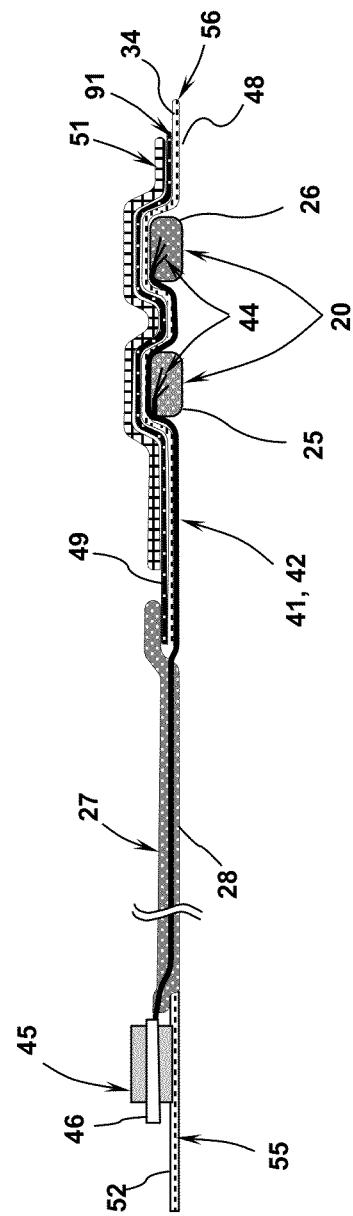
FIG. 8
FIG. 9

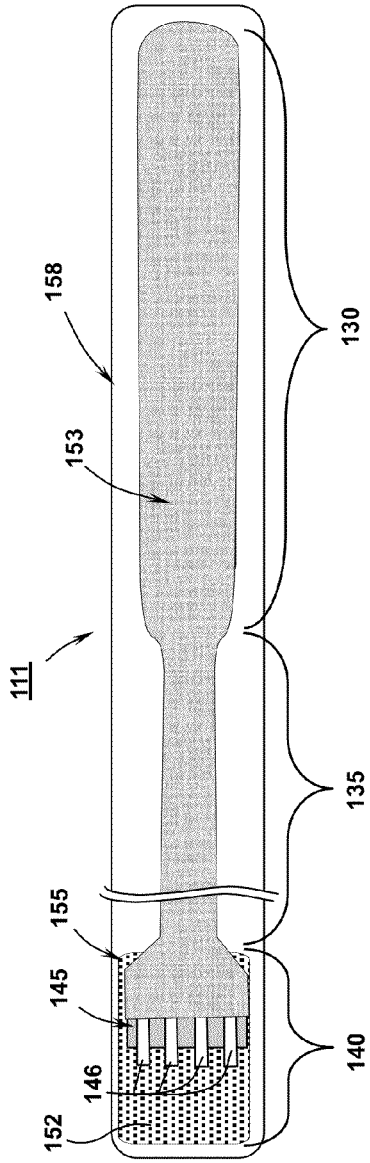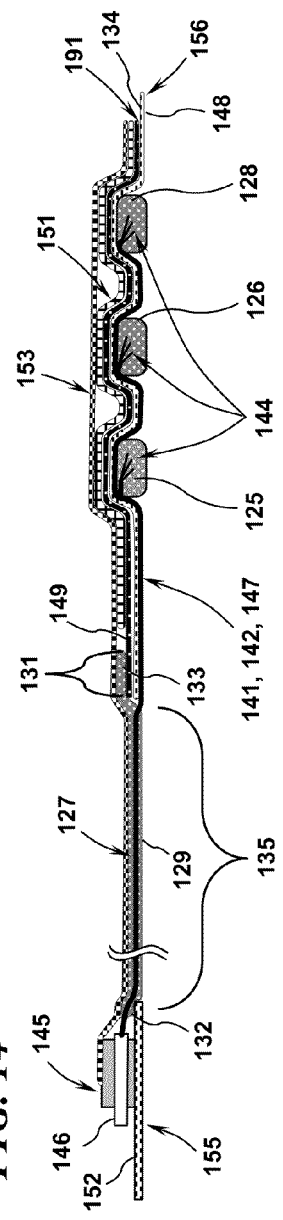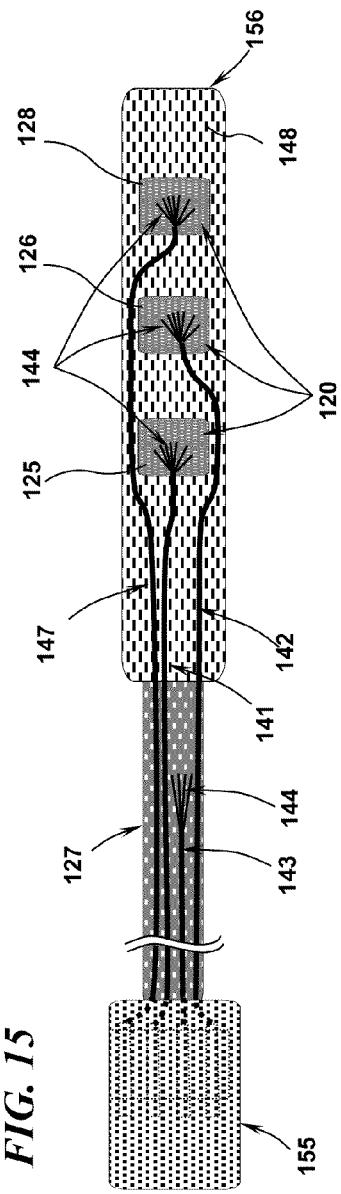

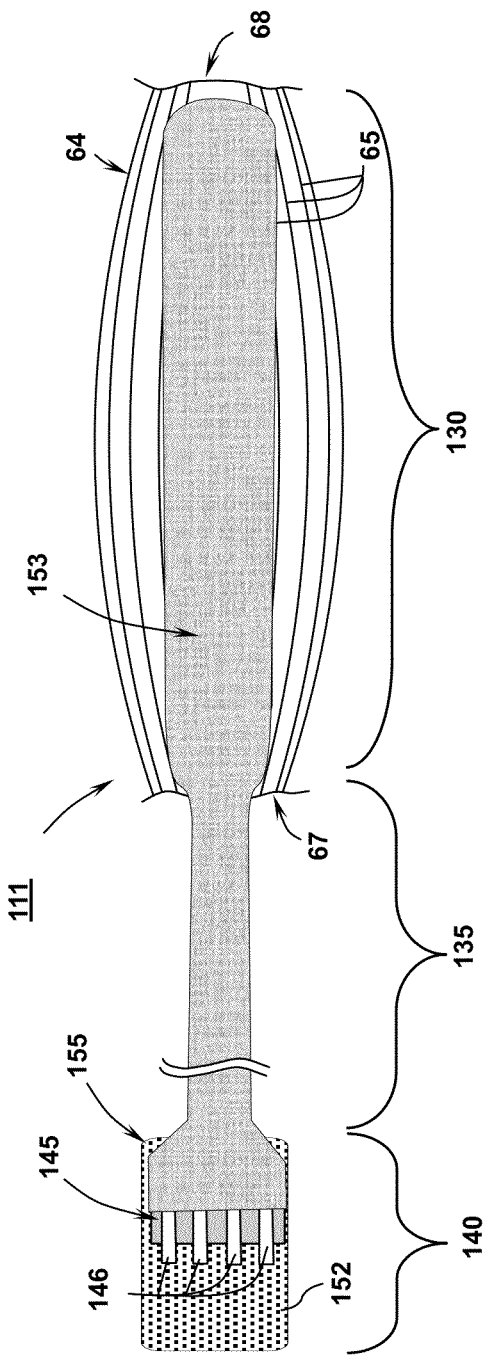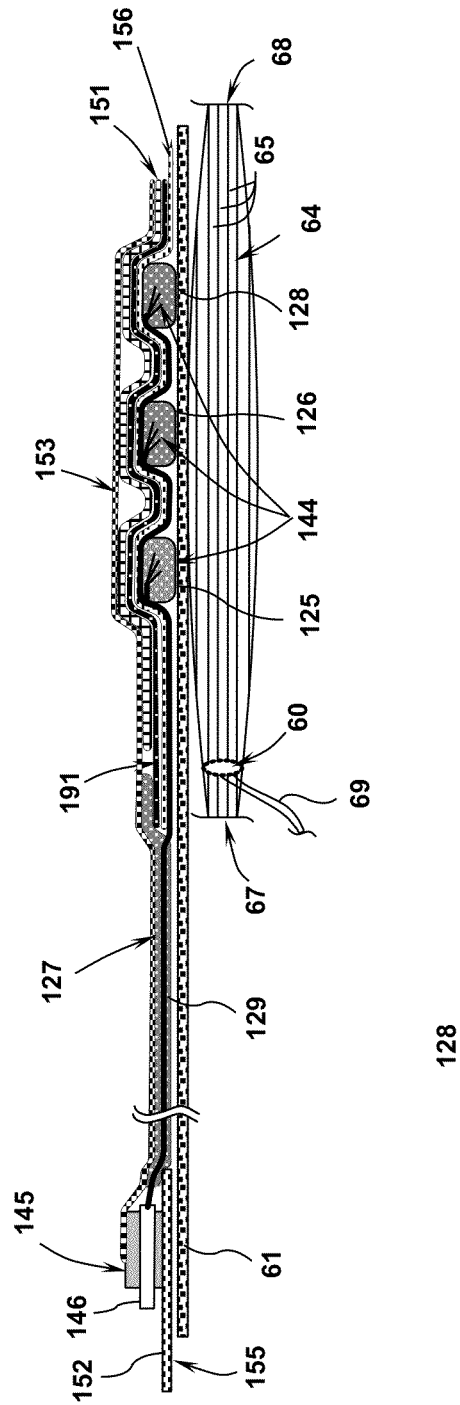

DISPOSABLE LOW-PROFILE CONFORMABLE BIOMEDICAL SENSOR

FIELD OF INVENTION

This application relates to the field of sensing bio-potentials generated within a living body and particularly relates to sensors placed on the surface of the skin for detecting the electrical activity from muscles using the surface Electromyographic (sEMG) signal.

BACKGROUND

Depolarization potentials created during a muscle fiber contraction generate an electrical field gradient that propagates in a direction along the fibers throughout the volume conductor comprised of the muscle, the surrounding tissue, and skin layers. Electrodes placed on the skins surface allow for the non-invasive detection of this electrical field gradient providing the temporal summation of the propagating depolarization potentials of the active muscle fibers in the underlying vicinity of the electrode. The resulting voltage on the skin is the sEMG signal.

In order to measure this voltage, an electrolytic interface is formed between the electrolytes in the subcutaneous tissue and the ohmic electrically conductive surface of the electrode contact attached to the skins surface. The primary electrical conduit between the subcutaneous volume conductor and the skins surface is established via the sweat ducts which pass through the non-conductive stratum corneum so that sweat and moisture from the underlying sweat glands are deposited onto the skins surface completing the electrolytic interface.

The electrolytic interface consists of disassociated ions from the electrolyte forming a layer on the conductive electrode contact surface (Nernst polarization or contact half-cell potential). Depending on the chemical composition, concentration of the electrolytes on the skin, and the composition of the electrode contact metal, the half-cell potentials can range in amplitude up to several hundred millivolts.

Signal potentials emanating from the muscle in the underlying tissue are conveyed via ionic transport through the electrolyte to the exposed conductive contact surface of the electrode.

The signal amplitude may be several orders of magnitude smaller than the half-cell potential and ranges from 10 microvolts to 5 millivolts. The resultant voltage sensed by the electrode contact is therefore the electrical summation of the signal potential and contact half-cell potential.

When the electrolytic skin interface of the electrode is mechanically disturbed due to relative movement or pressure changes between the tissue and conductive surface of the electrode, the effective concentration of the electrolytes can be altered so that the resultant half-cell potential amplitude is modulated by the mechanical disturbance. The modulation of hall-cell potential is termed "movement artifact" and typically arises from rapid body movements, or objects or clothing coming into contact with the sensor case housing the electrodes.

Movement artifact can be particularly problematic as the change in half-cell potential can exhibit large (>50 mV) voltage deviations which overwhelm the amplitude of the sEMG signal.

An additional source of movement artifact is due to the triboelectric charge that can accumulate on the non-conducting stratum corneum as a result of walking on carpet or contact with certain fabrics under low humidity conditions. This effect can be especially problematic when the electrolytic skin interface exhibits high impedance resulting from the lack of suitable moisture between the electrode contact and the skin. This impedance can reach tens of megohms for contacts with an area of 1 mm squared placed on unprepared skin.

Common teaching dictates that the configuration of a sensor designed to detect sEMG signals consists of two electrode contacts placed on the skin over the muscle and oriented in a direction parallel to the muscle fibers. A third "reference" contact is preferentially located at an electrically inactive location on the body. Characteristically, disposable sEMG sensors preferentially designed for clinical use consist of two electrodes filled with skin impedance reducing electrolytic gel or formed from hydrophilic gel; one for each signal input placed singularly, or in pairs, mounted on a flexible non-conductive pad adhered to the skin over the muscle. In some sensors the two signal and reference contacts are placed on the same insulating pad in the form of an equilateral triangle.

The electrodes are attached by snaps or spring loaded clips and connected to remote electronic circuitry via individual lead wires. The preferred recording configuration is the single differential configuration where the voltage at each signal input contact is measured with respect the third reference contact and subtracted using a differential pre-amplifier circuit. In this way, any voltages common to both electrodes such as half-cell potentials and line interference effectively subtract to zero for an ideal amplifier.

However, in some disposable, single use, sEMG electrode designs, disturbances to the electrode interface induced from contact forces applied directly to the interface or induced from shear forces applied to the interface through the snap leads and interconnection cable movement are likely to cause an unequal localized disruption of the electrolyte junction half-cell potential of each signal electrode contact. This unequal change in half-cell potentials can not be removed by differential subtraction and as a result generates a movement artifact signal.

Additionally, a foam-backed disposable sensor interface may be susceptible to triboelectric charges that can accumulate on the non-conducting stratum corneum as a result of walking on carpet or contact with certain fabrics under low humidity conditions. The problems of movement artifact and sensitivity to electro-static fields are especially severe when the sensor is placed under clothing garments.

As further background, some reusable tethered and wireless sensor designs address the issue of movement and electrostatic artifact suppression by utilizing an enclosed, shielded case incorporating integrated preamplifier circuitry with signal and reference electrode contacts secured to the bottom. These sensors are placed directly on the muscle of interest and eliminate signal lead cable artifacts, however, their larger sensor dimensions and mass may preclude their placement on multiple, smaller adjacent muscles. Compared to disposable, single use configurations, reusable sensors also incur the additional steps of sanitizing procedures for repeated use in the clinical environment.

All of the aforementioned electrode contact and sensor configurations described as prior art offer only a limited set of solutions for detecting high fidelity sEMG signals in applications involving dynamic contractions. Disposable, single use configurations are convenient to apply and provide a hygienic implementation for clinical applications. However, their susceptibility to electrode and cable induced movement artifact precludes their use in vigorous applications and during conditions where electro-static fields may be generated such as sensor placement under an individual's clothing. Reusable, encased sensor designs with active electronics can suppress artifacts by eliminating the signal lead cables and by stabilizing the electrodes, yet lack compliance to fit to the contours of smaller underlying muscles which may encumber muscle movement during large flexions and extensions during vigorous dynamic activities.

The single differential recording configuration is most commonly used in both disposable and re-useable sensor designs. While suitable for the general evaluation of muscle activity, the single differential configuration is susceptible to the signal crosstalk interference generated from nearby active muscles. This precludes its use in applications requiring measurement of concurrent isolated muscle activity from multiple, adjacently located muscle groups. These applications are diverse and can range from sports and ergonomic activities to the clinical evaluation of patients with gait problems, Parkinson's disease, and other motor disorders. The double differential sensor configuration offers a potential solution for minimizing the effect of signal crosstalk in these applications. The technique uses an additional differential amplifier to subtract out the predominately in-phase crosstalk signal components present in both signal outputs of two differentially amplified contact pairs. However, the requirement of additional electrode contacts, increased sensor area, and more complex electronic circuitry has precluded its general acceptance.

It would be an improvement in the art to provide a disposable adhesive sensor configuration with integrated lead cable which can mold to the contours of the skin, which can comply with skin movement, and which can suitably isolate and detect muscle signals while suppressing movement artifacts and the effects of electro-static fields. When configured into a multi-sensor array, these low-profile, low-mass sensors would be applicable to the unencumbered measurement of muscle activity from multiple adjacent muscles, especially from smaller muscles such as those located in the face, neck, and hand. It could be used in conjunction with both existing tethered and wireless sensor technologies utilizing single and double differential recording configurations.

SUMMARY

According to the system described herein, a biomedical sensor that provides an electrode to body interface includes a plurality of individual electrically conductive, adhesive, cross-linked hydrophilic polymer gel substrate layers which form a plurality of signal detection electrode contacts and an elongated electrically conductive polymer reference electrode contact, a plurality of insulated conductor leads electrically connected to the electrode contacts and extending away from the electrode contacts, the leads being embedded and fully enveloped lengthwise within the elongated electrically conductive hydrophilic polymer reference electrode contact to form a lead cable shielding the sensor and leads from external electrical fields and suppressing movement artifact while providing a conformable, contoured attachment of the sensor and lead cable to underlying skin of the body, and a conformable framework mechanically supporting and electrostatically shielding the insulated conductor leads and electrode contacts. Each electrically conductive, adhesive, cross-linked hydrophilic polymer gel signal detection electrode contact may be disposed on and retained by a body-directed insulating substrate layer of a double-sided adhesive sheet. An electrically conductive electro-static shield substrate layer may be adhered to and retained by an upper surface of the insulating substrate of the double-sided adhesive, and contoured to match a profile of an underlying substrate to make mechanical and electrical contact with the electrically conductive, adhesive, cross-linked hydrophilic polymer gel reference contact. The electro-static shield substrate layer may be formed from an electrically conductive metallic sheet. The electro-static shield substrate layer may be formed from an electrically conductive plastic sheet. The electro-static shield substrate layer may be formed from an electrically conductive hydrophilic polymer gel. A malleable stabilizing substrate may be adhered to and retained by the upper surface of the electrically conductive shield substrate and contoured to match the profile of the underlying substrate layer thereby supporting the underlying electrode contacts. An insulated, conformable top covering layer contoured to follow a perimeter outline of the sensor may be adhered to and may conform to top surfaces of the sensor. The conformable top covering layer may be cosmetically textured and colored to more closely match color and texture of the underlying skin. The electrically conductive, adhesive, cross-linked hydrophilic polymer gel substrate layers may be configured as a plurality of signal detection contacts and one reference contact, each having a respective length of insulated conductor lead which mechanically and electrically terminates in the contacts of a connector block. The insulated conductor leads for each of the signal and reference contacts may be formed with one or more strands of electrically conductive wire. The insulated conductor leads for each of the signal and reference contacts may be formed from electrically conductive printed circuit traces on a conformable insulating substrate. The terminating printed circuit traces from each of the conductor leads may be shaped and retained on a rigid substrate to form connector contacts. A region of the respective insulated conductor leads for each of the signal and reference contacts may be un-insulated and embedded within the upper surface of the electrically conductive, adhesive, cross-linked hydrophilic polymer gel to make an electrical contact. Each of the electrically conductive areas of the signal contacts may be formed from a sheet of electrically conductive, adhesive, cross-linked hydrophilic polymer gel in the shape of a rectangle with a bottom surface aligned in parallel and coplanar with a body-directed insulating adhesive substrate. Each of the electrically conductive areas of the signal contacts may be formed from a sheet of electrically conductive, adhesive, cross-linked hydrophilic polymer gel in a shape of a disc with a bottom surface aligned in parallel and coplanar with a body-directed insulating adhesive substrate. The reference contact may be formed from a sheet of electrically conductive, adhesive, cross-linked hydrophilic polymer gel in the shape of an elongated rectangular strip aligned linearly and in a plane of the signal contacts and extending away from the signal contacts so as to form a separate length of conducting reference electrode surface. The insulated conductor leads exiting from each of the contacts may be embedded and fully enveloped along a length of the elongated electrically conductive, adhesive, cross-linked hydrophilic polymer gel reference contact to form a lead cable terminating in contacts of a connector block. The electrically conductive contact areas may form a linear array of two symmetrically spaced signal contacts that detect signals using a differential recording technique. The electrically conductive signal areas may be arranged to form a sensor array having multiple linear array elements that detect signals from multiple detection sites using one or more single differential sensor configurations and double differential sensor configurations. The electrically conductive signal areas may form a linear array of three symmetrically spaced signal contacts that reduce crosstalk signals using a double differential recording technique. The electrically conductive signal areas may be arranged to form a sensor array having multiple linear array elements that detect signals from multiple detection sites using one or more single differential sensor configurations and double differential sensor configurations. The sensor may be single use and disposable.

The system described herein is a biomedical sensor including; a planar framework of component layers supporting an arrangement of insulated conductor leads whose terminating un-insulated, electrically conductive surfaces are embedded within multiple electrically conductive, adhesive, cross-linked hydrophilic polymer gel surfaces projecting from the body-directed surface to form signal detection electrode and reference electrode contacts, an electrostatic shield component, an electrode stabilization component, and an interconnection cable component. The interconnection cable component is formed by embedding each of the insulated conductor leads within the elongated section of the reference electrode so that they are fully enveloped and electrically shielded by the conductive polymer gel. The mechanical and electrical configurations of the framework act in synergy to shield the sensor contacts and lead cable from external electrical fields and suppress movement artifact while providing a flexible, contoured fit of the sensor and cable to the underlying skin.

The system described herein relates to an improved type of multi-electrode, disposable, adhesive sensor configuration and adhesive lead cable that can mold to the contours of the underlying musculature and flex with skin movement while suppressing movement artifact. Unlike the existing designs of typical disposable multi-electrode sensors with snap connectors or separate floating lead wires which must be taped to the skin and introduce cable motion artifact, the system described herein incorporates an elongated strip of conformable, electrically conductive, adhesive, cross-linked hydrophilic polymer gel with integrated lead wires forming a cable which self-adheres to the skin, shields the leads from external electrical interference, and cushions the leads from mechanical artifact. Furthermore, the low profile planar framework of the system described herein contains a malleable component which is pliable to the extent that it can be manually shaped to match the contour of the underlying musculature yet is rigid enough to mechanically stabilize the area under the signal electrode contacts so that they react similarly, and in unison to the electrical artifact manifestation of an applied mechanical disturbance in such a way that the resulting common electrical components of the artifact can be canceled out by a differential sensing circuit configuration.

According to one feature of the system described herein, the arrangement of contacts may be configured as a planar array of multiple signal detection electrode contact surfaces, and one reference electrode contact surface, each with a respective insulated conductor lead which mechanically and electrically terminates in the contacts of a connector block providing individual signal and reference input connections to preamplifier circuitry.

According to another feature of the system described herein, the array may be configured as a linear arrangement of contacts consisting of two signal detection contact surfaces, and one reference contact surface, each with a respective insulated conductor lead which mechanically and electrically terminates in the contacts of a connector block providing individual signal and reference input connections to a differential preamplifier circuit configuration.

According to another feature of the system described herein, the array may be configured as a linear arrangement of contacts consisting of three signal detection contact surfaces, and one reference contact surface, each with a respective insulated conductor lead which mechanically and electrically terminates in the contacts of a connector block providing individual signal and reference input connections to a double differential preamplifier circuit configuration.

According to another feature of the system described herein, each of the conductive areas of the signal detection contact surface may be formed from a sheet of electrically conductive, adhesive, cross-linked hydrophilic polymer gel in the shape of a rectangle with the bottom surface aligned and coplanar with the body-directed insulating adhesive substrate.

According to another feature of the system described herein, each of the conductive areas of the signal detection contact surface may be formed from a sheet of electrically conductive, adhesive, cross-linked hydrophilic polymer gel in the shape of a disc with the bottom surface aligned and coplanar with the body-directed insulating adhesive substrate.

According to another feature of the system described herein, the insulated conductor leads for each of the signal detection and reference contact surfaces may be formed from one or more strands of conductive wire.

According to another feature of the system described herein, the conductor leads for each of the signal detection and reference contact surfaces, and connectors of the connector block may be formed from conductive printed circuit traces on a conformable insulating substrate.

According to another feature of the system described herein, a region of the respective insulated conductor lead for each of the signal detection and reference contact surfaces may be un-insulated and embedded in the upper surface of their respective electrically conductive, adhesive, cross-linked hydrophilic polymer gel to make an electrical connection with the gel.

According to another feature of the system described herein, each of the electrically conductive areas of the signal detection contacts may be retained by a body-directed insulating substrate of double-sided adhesive.

According to another feature of the system described herein, the reference electrode contact surface may be formed from a sheet of electrically conductive, adhesive, cross-linked hydrophilic polymer gel in the shape of an elongated rectangular strip aligned linearly and in the plane of the signal contacts and extending away from the signal contacts so as to form a separate length of conducting reference electrode surface.

According to another feature of the system described herein, the insulated conductor leads exiting from each of signal and reference contacts may be embedded and fully enveloped within the elongated body of the electrically conductive, adhesive, cross-linked hydrophilic polymer gel reference contact along its length to form a lead cable terminating in the contacts of a connector block.

According to another feature of the system described herein, an electrically conductive electro-static shield substrate layer may be adhered to the upper surface of the insulating substrate of double-sided adhesive and contoured to match the profile of the underlying substrate so that it makes mechanical and electrical contact with the electrically conductive, adhesive, cross-linked hydrophilic polymer gel reference contact.

According to another feature of the system described herein, the electro-static shield substrate layer may be an electrically conductive metallic sheet.

According to another feature of the system described herein, the electro-static shield substrate layer may be an electrically conductive plastic sheet.

According to another feature of the system described herein, the electro-static shield substrate layer may be formed by an extension of the hydrophilic polymer gel reference contact.

According to yet another feature of the system described herein, a malleable stabilizing substrate may be adhered to the upper surface of the electrically conductive shield substrate and contoured to match the profile of the underlying substrate layers.

According to another feature of the system described herein, an insulated, conformable top covering contoured to match the profile and follow the perimeter outline of the sensor may be adhered to the top surface of the terminal block, reference contact and stabilizing substrate of the sensor.

According to another feature of the system described herein, the conformable top covering may be cosmetically textured and colored so that it more closely matches the color and texture of the underlying skin.

According to another feature of the system described herein, a body-directed substrate of double-sided adhesive may be adhered to the bottom surface of the connector block providing means for mounting the connector block on the skin.

According to another feature of the system described herein, the body-directed surfaces of the sensor may be mounted on a release liner.

According to another feature of the system described herein, the sensor may be single use and disposable.

DESCRIPTION OF THE DRAWINGS

These and other features of the system described herein will become more apparent upon perusal of the following description taken in conjunction with the accompanying drawings wherein:

FIG. 1 is a top view of a biomedical sensor according to the system described herein;

FIG. 2 is a cross-sectional view of the sensor shown in FIG. 1 according to the system described herein;

FIG. 3 is a bottom and cross-sectional cable view of the sensor shown in FIG. 1 according to the system described herein;

FIG. 7A is a top view of the sensor shown in FIG. 4A with the electro-static shield of hydrophilic polymer gel substrate layer added according to the system described herein;

FIG. 7B is a cross-sectional view of the sensor shown in FIG. 7A according to the system described herein;

FIG. 8 is a top view of the sensor shown in FIG. 6A with the malleable stabilizing substrate layer added according to the system described herein;

FIG. 9 is a cross-sectional view of the sensor shown in FIG. 8 according to the system described herein;

FIG. 13 is a top view of another biomedical sensor embodiment according to the system described herein;

FIG. 14 is a cross-sectional view of the sensor shown in FIG. 13 according to the system described herein;

FIG. 15 is a bottom view of the sensor shown in FIG. 13 according to the system described herein;

FIG. 16 is a schematic top view of the sensor of FIG. 13 mounted adjacent to a bundle of muscle fibers according to the system described herein;

FIG. 17 is a schematic side view of the sensor of FIG. 13 mounted adjacent to a bundle of muscle fibers according to the system described herein;

DESCRIPTION OF VARIOUS EMBODIMENTS

Figure 4A:
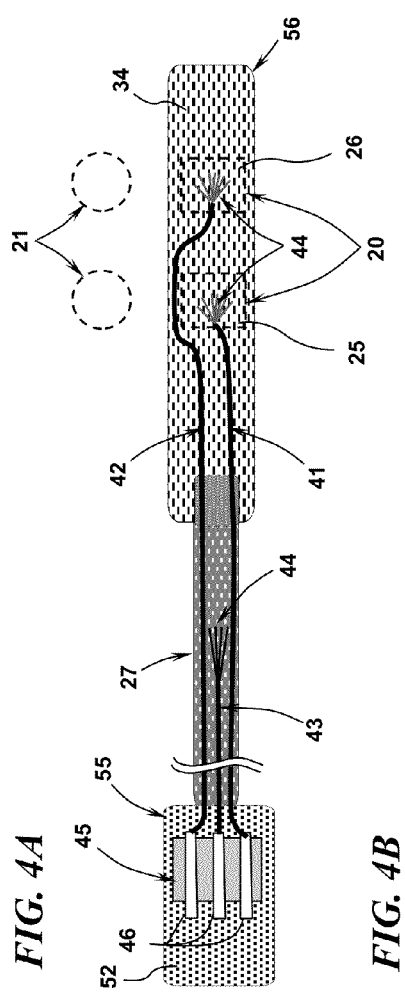
FIG. 4A is a top view of the sensor shown in FIG. 1 showing the body-directed substrate layer with signal and reference contacts and alternative disc electrode contact arrangement according to the system described herein.

A biomedical sensor 11 includes a connector region 40, a lead cable region 35, and a sensor head region 30, all overlaid with a top covering 53, and disposed on a release liner 58 as illustrated in the top view of FIG. 1. Cross-sectional profile and bottom views of sensor 11 are shown in FIGS. 2 and 3. The connector region 40 consists of electrical contacts 46 retained in a connector block 45 disposed on the top surface 52 of a double-sided adhesive substrate 55. Each of the contact terminals 46 electrically terminates their respective signal detection conductor leads 41, 42 and reference conductor lead 43 for connection to external preamplifier circuitry. Attached to the top surface 52 of substrate 55 is one end 32 of an, electrically conductive, adhesive, cross-linked hydrophilic polymer gel reference contact 27 with a body-directed surface 28, and within which the insulated signal detection conductor leads 41, 42, and insulated reference conductor lead 43 are embedded and fully enveloped along its length forming the lead cable region 35 and as further illustrated in FIG. 3 showing a bottom view of sensor 11 and a cross-section of reference contact 27 with embedded insulated conductor leads 41, 42 43. The opposing end 33 of the reference contact 27 and insulated signal conductor leads 41, 42 are incorporated within the sensor head region 30. The sensor head region 30 is a multi-layer composite comprised of a double-sided insulating adhesive sheet interface substrate 56 retaining a pair of electrically conductive, adhesive, cross-linked hydrophilic polymer gel signal detection contacts 20, an electro-static shield substrate 91 attached to the upper surface 34 of the interface 56, and a malleable stabilizing substrate 51 attached to the upper surface 49 of shield substrate 91 as illustrated in the cross-sectional view FIG. 2.

Figure 4B:
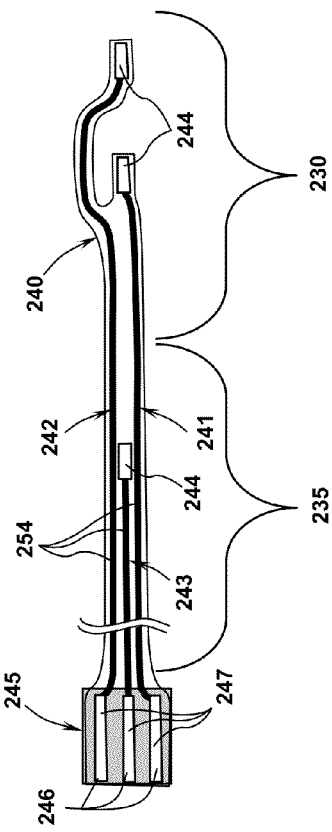
FIG. 4B is a top view of the alternative printed circuit conductor lead arrangement for the sensor shown in FIG. 4A according to the system described herein.
Figure 5:
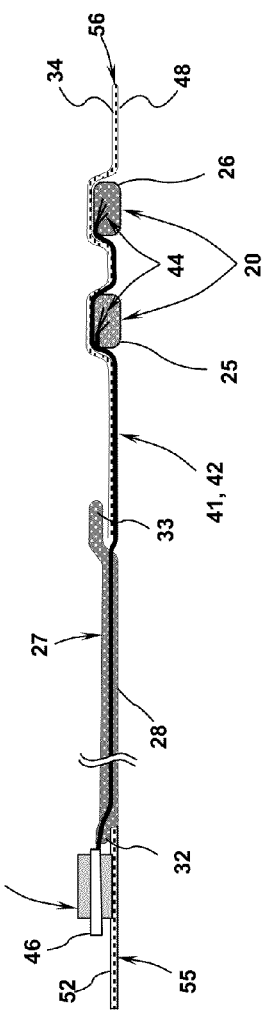
FIG. 5 is a cross-sectional view of the sensor shown in FIG. 4A according to the system described herein.

The constructional architecture of sensor head region 30 is detailed in the following pairs of figures which show the top and cross-sectional views of each subsequently added substrate layer:

FIG. 4A and FIG. 5 show the double-sided adhesive substrate layer 56 retaining a pair of electrically conductive, adhesive, cross-linked hydrophilic polymer gel signal detection contacts 20 and associated insulated conductor leads 41, 42. The pair of contacts 20 is comprised of a positive signal detection contact 25 and a negative signal detection contact 26 disposed on the body-directed surface 48 of layer 56 and linearly aligned with respect to the reference contact 27. An alternative signal detection contact arrangement in the form of disc shaped contacts 21 is also shown in FIG. 4A. The un-insulated region 44 of each of the insulated conductor leads 41, 42 is embedded within their respective polymer signal electrode contacts 25, 26 so as to form an electrical inter-connection between the signal detection contacts 20 and the electrical contact terminals 46 of connector block 45. Similarly, the un-insulated region 44 of insulated conductor lead 43 is embedded within the polymer reference electrode contact 27 so as to form an electrical inter-connection between the reference contact 27 and the electrical contact terminals 46 of connector block 45. An alternative flexible printed circuit inter-connection arrangement is shown in FIG. 4B consisting of an insulated printed circuit substrate 240 and printed circuit traces 254 forming the insulated conductor leads 241, 242, 243 and connector terminals 246. The sensor head region 230 of the printed circuit substrate 240 is retained on body-directed surface 48 of layer 56. The exposed un-insulated regions 244 are embedded in the electrode contacts 25, 26, and reference contact 27. The un-insulated region 247 of connector terminal traces 246 of the printed circuit 240 are mounted on a connector block 245. The lead cable region 235 of printed circuit substrate 240 is embedded and enveloped within the reference contact substrate 27.

Figure 6A:
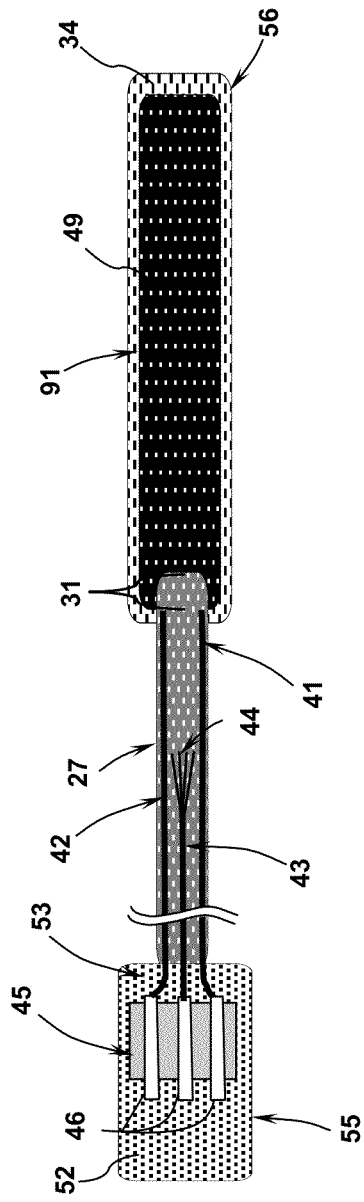
FIG. 6A is a top view of the sensor shown in FIG. 4A with the electro-static shield substrate layer added according to the system described herein.
Figure 6B:
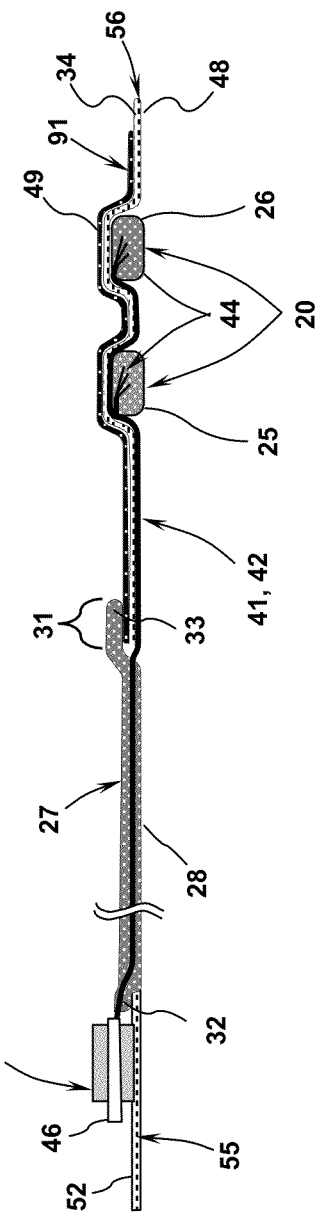
FIG. 6B is a cross-sectional view of the sensor shown in FIG. 6A according to the system described herein.

FIGS. 6A and 6B illustrate the next added constructional layer comprised of an electrically conductive electro-static shield substrate 91 disposed on and adhered to the upper surface 34 of the interface 56 forming a mechanical and electrical connection with the contacting overlapping surface 31 of the electrically conductive polymer reference contact 27.

FIGS. 7A and 7B show an alternative arrangement where the electrostatic shield substrate 91 is formed by extending the electrically-conductive polymer reference contact 27 to adhere to the upper surface 34 of the insulating substrate 56 and contoured to match the profile of substrate 56 so that the substrate 91 makes mechanical contact. The use of electrically-conductive polymer as an electrostatic shield substrate 91 provides a compliant cushion to reduce the effects of mechanically-induced artifact.

FIGS. 8 and 9 illustrate the next constructional layer comprised of a malleable stabilizing substrate 51 disposed on and adhered to the upper surface 49 of shield substrate 91 supporting and stabilizing the sensor head region 30. The malleable substrate 51 is pliable to the extent that it can be manually shaped to match the contour of the underlying musculature, yet is rigid enough to mechanically stabilize the area underlying the signal detection contact surfaces 25, 26 so that they both react similarly, and in unison to the electrical artifact manifestation of an applied mechanical disturbance.

Figure 10:
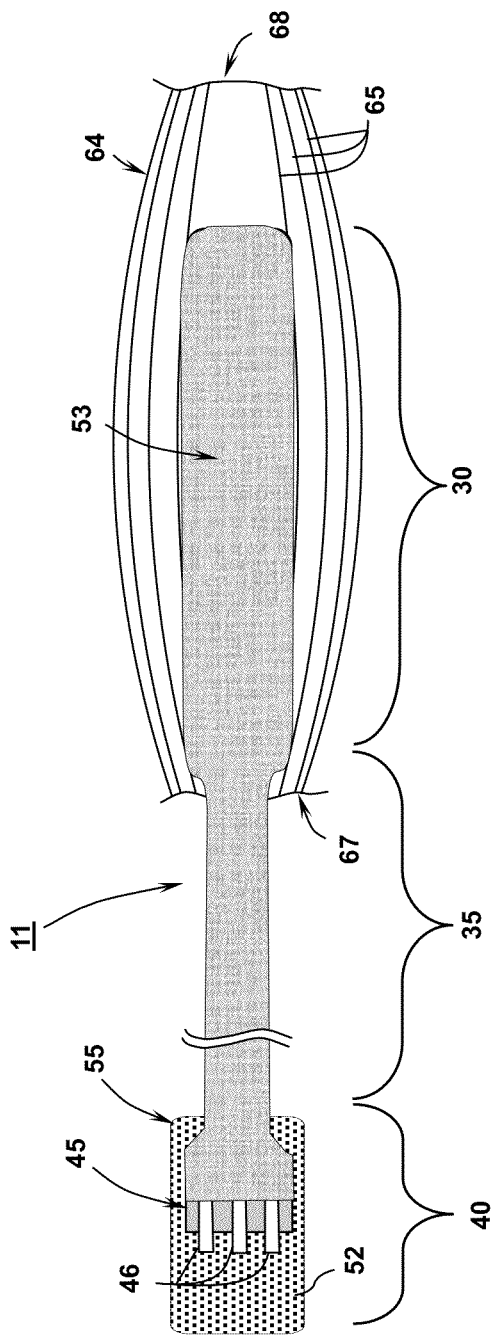
FIG. 10 is a schematic top view of the sensor of FIG. 1 mounted adjacent to a bundle of muscle fibers according to the system described herein.
Figure 11:
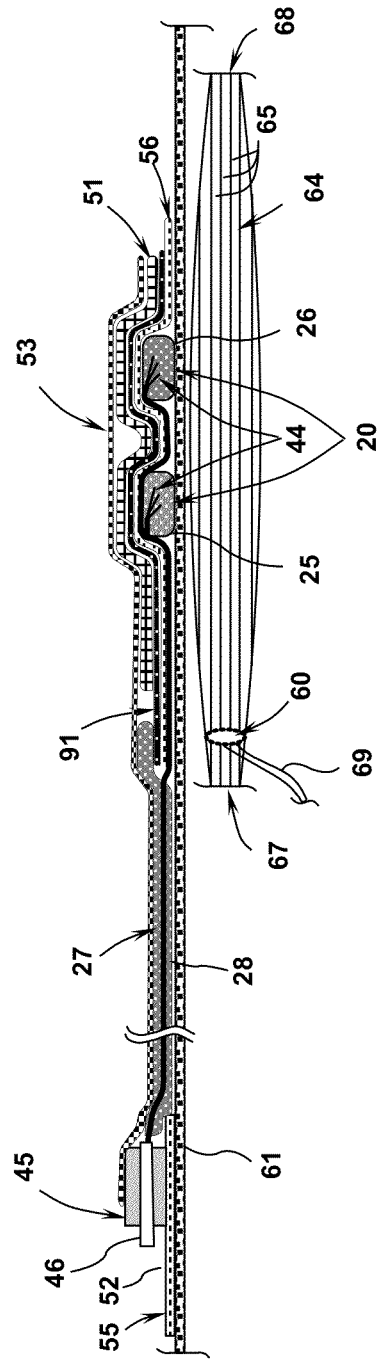
FIG. 11 is a schematic side view of the sensor of FIG. 1 mounted adjacent to a bundle of muscle fibers according to the system described herein.

Prior to use, the release liner 58 is removed from the sensor 11. Next, the adhesive substrates 55, 56 and reference contact surface 27 are adhered to the skin 61 of the subject orienting the long axis of the sensor head region 30 so that the pair of contacts 20 are aligned in parallel with respect to the muscle fibers 65 and centered with respect to the proximal 67 and distal 68 ends of muscle bundle 64, with the lead cable 35 and connector 40 regions pointed away in a proximal direction with respect to the proximal end 67 of bundle 64 as shown in the top view of FIG. 10 and cross-section view of FIG. 11. That arrangement of the sensor 11 establishes a known positive potential for the detection contact 25 and a negative potential for the detection contact 26.

Figure 12:
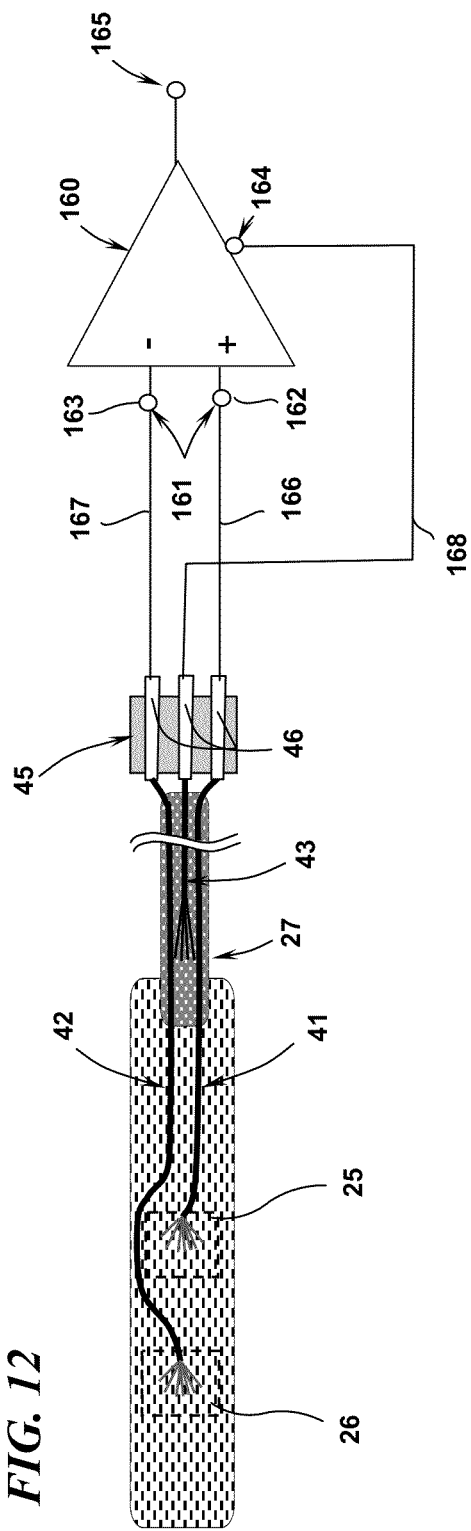
FIG. 12 is a schematic diagram of the single differential amplifier recording configuration of the sensor of FIG. 1 according to the system described herein.

A schematic diagram of the preferred differential preamplifier recording configuration used with sensor embodiment 11 is shown in FIG. 12. A high impedance differential preamplifier 160 with differential inputs 161 consisting of a positive input 162 and a negative input 163, and a reference input 164 is connected to the signal detection contacts 25, 26 and reference contact 27 using interconnections 166, 167, 168 attached to the their respective conductor leads 41, 42, 43 terminated in the contacts 46 of connector block 45. The signal output 165 is the arithmetic difference between the signal detected at contacts 25 and 26 measured with respect to the reference contact 27.

Another biomedical sensor embodiment 111 includes a connector region 140, a lead cable region 135, and a sensor head region 130, all overlaid with a top covering 153, and disposed on a release liner 158 as illustrated in the top view of FIG. 13. Cross-sectional profile and bottom views of sensor 111 are shown in FIGS. 14 and 15. The connector region 140 consists of electrical contacts 146 retained in a connector block 145 disposed on the top surface 152 of a double-sided adhesive substrate 155. Each of the contact terminals 146 electrically terminates their respective signal detection conductor leads 141, 142, 147 and reference conductor lead 143 for connection to external preamplifier circuitry. Attached to the top surface 152 of substrate 155 is one end 132 of an electrically conductive, adhesive, cross-linked hydrophilic polymer gel reference contact 127 with a body-directed surface 129 and within which the insulated signal detection conductor leads 141, 142, 147 and insulated reference conductor lead 143 are embedded and fully enveloped along its length forming the lead cable region 135. The opposing end 133 of the reference contact 127 and insulated signal conductor leads 141, 142, 147 are incorporated within the sensor head region 130. The sensor head region 130 is a multi-layer composite comprised of a body-directed substrate 156 retaining signal detection contacts 120, an electro-static shield substrate 191, and a malleable stabilizing substrate 151. The body-directed substrate layer 156 of sensor 111 consists of a double-sided adhesive sheet retaining an array of three electrically conductive, adhesive, cross-linked hydrophilic polymer gel signal detection contacts 120 and associated insulated conductor leads 141, 142, 147. The three contacts 120 are comprised of a positive signal detection contact 125, a shared positive/negative signal detection contact 126, and a negative signal detection contact 128 disposed on the body-directed surface 148 of layer 156 and linearly aligned with respect to the reference contact 127. The un-insulated region 144 of each of the insulated conductor leads 141, 142, 147 is embedded within their respective polymer signal detection contacts 125, 126, 128 so as to form an electrical inter-connection between the signal detection contacts 120 and the electrical contact terminals 146 of connector block 145. Similarly, the un-insulated region 144 of insulated conductor lead 143 is embedded within the polymer reference electrode contact 127 so as to form an electrical inter-connection between the reference contact 127 and the electrical contact terminals 146 of connector block 145. The electrically conductive electro-static shield substrate layer 191 of sensor 111 is disposed on and adhered to the upper surface 134 of the interface 156 forming a mechanical and electrical connection with the contacting overlapping surface 131 of the electrically conductive polymer reference contact 127. The malleable substrate layer 151 of sensor 111 is disposed on and adhered to the upper surface 149 of shield substrate 191. The malleable substrate 151 is pliable to the extent that it can be manually shaped to match the contour of the underlying musculature, yet is rigid enough to mechanically stabilize the area underlying the signal detection contact surfaces 125, 126, 128 so that they all react similarly, and in unison to the electrical artifact manifestation of an applied mechanical disturbance.

Prior to use, the release liner 158 is removed from the sensor 111. Next, the adhesive bottom surfaces 155, 156 and reference contact surface 127 are adhered to the skin 61 of the subject orienting the long axis of the sensor head region 130 so that the three contacts 120 are aligned in parallel with respect to the muscle fibers 65 and centered with respect to the proximal 67 and distal 68 ends of muscle bundle 64 with the lead cable 135 and connector 140 regions pointed away in a proximal direction with respect to the proximal end 67 of bundle 64 as shown in the top view of FIG. 16 and cross-section view of FIG. 17. That arrangement of the sensor 111 establishes the proper orientation of the three contacts 120 so that contact pairs 125, 126 and contact pairs 126, 128 equally detect the propagating field gradient of the sEMG signal.

Figure 18:
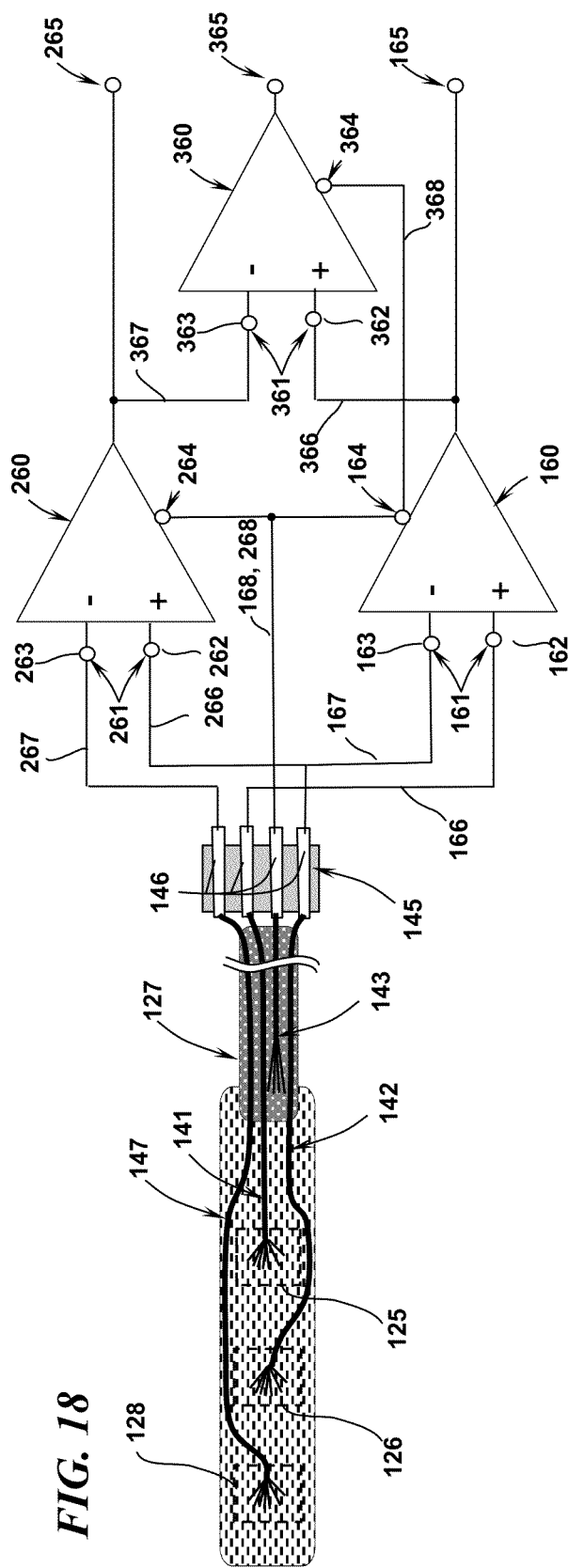
FIG. 18 is a schematic diagram of the double differential amplifier recording configuration of the sensor of FIG. 13 according to the system described herein.

A schematic diagram of the preferred double differential preamplifier recording configuration used with sensor embodiment 111 is shown in FIG. 18. The double differential preamplifier configuration consists of three high impedance differential preamplifiers 160, 260, 360. Differential preamplifier 160 with differential inputs 161 consisting of a positive input 162 and a negative input 163, and a reference input 164 is connected to the signal detection contacts 125, 126 and reference contact 127 using interconnections 166, 167, 168 attached to the their respective conductor leads 141, 142, 143 terminated in the contacts 146 of connector block 145. The single differential signal output 165 is the arithmetic difference between the signal detected at contacts 125 and 126 measured with respect to the reference contact 127. Differential preamplifier 260 with differential inputs 261 consisting of a positive input 262 and a negative input 263, and a reference input 264 is connected to the signal detection contacts 126, 128 and reference contact 127 using interconnections 266, 267, 268 attached to the their respective conductor leads 142, 147, 143 terminated in the contacts 146 of connector block 145. The single differential signal output 265 is the arithmetic difference between the signal detected at contacts 126 and 128 measured with respect to the reference contact 127. Differential preamplifier 360 with differential inputs 361 consisting of a positive input 362 and a negative input 363, and a reference input 364 is connected to the single differential signal outputs 165, 265 and references 164, 264 of preamplifiers 160, 260 using interconnections 366, 367, 368. The double differential signal output 365 is the arithmetic difference between the single differential output 165 and the single differential output 265.

Figure 19:
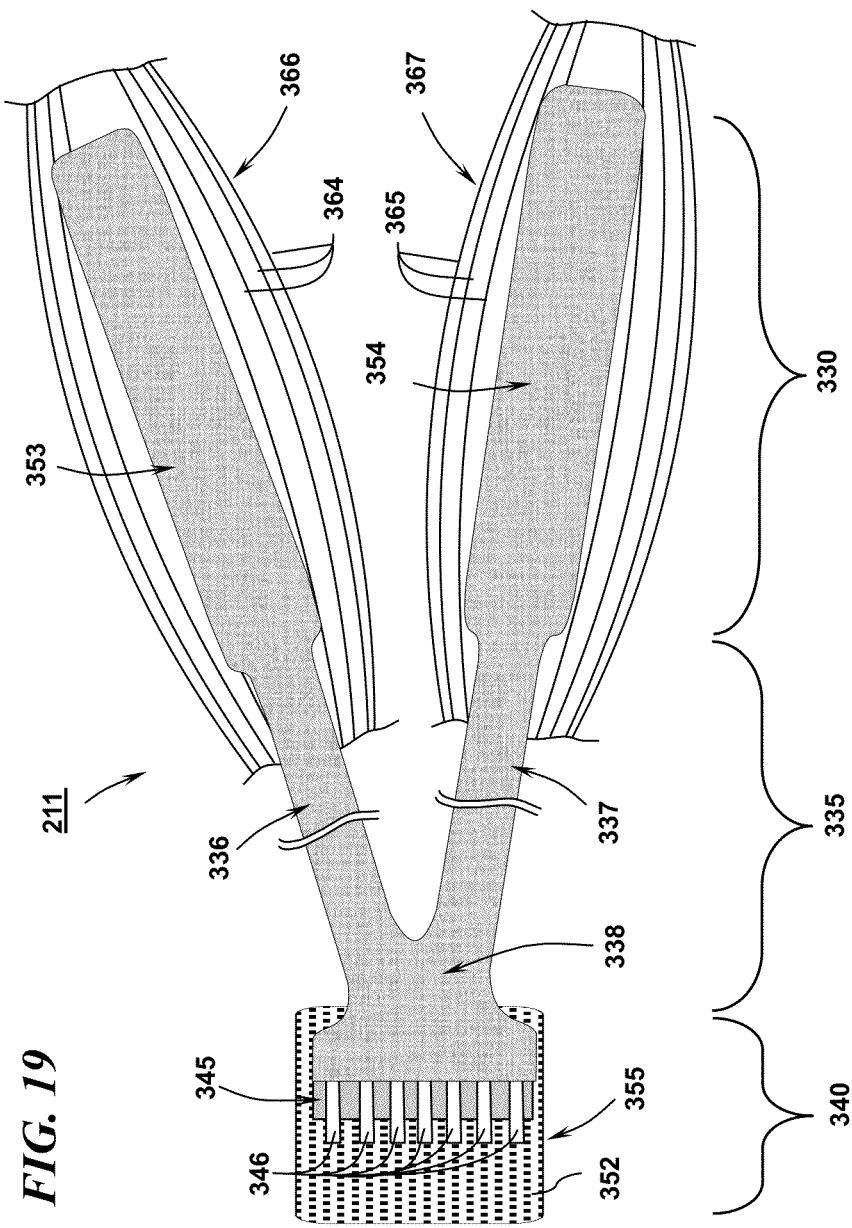
FIG. 19 is a top view of another biomedical sensor embodiment of the invention forming a multi-sensor array according to the system described herein.

Another biomedical sensor embodiment 211 includes a connector region 340, a lead cable region 335, and sensor head region 330 comprised of multiple independent sensor heads 353 and 354 which form a sensor array as shown in the top view of FIG. 19. For illustrative purposes, FIG. 19 depicts an array consisting of two sensor heads 353 and 354 positioned adjacent to one another, however the total number of sensor heads in the array, their relative positioning, and alignment are not constrained and can be tailored to specific applications.

The connector region 340 consists of electrical contacts 346 retained in a connector block 345 disposed on the top surface 352 of a double-sided adhesive substrate 355. Each of the contact terminals 346 electrically terminates their respective signal detection conductor and reference conductor leads of sensor heads 353 and 354 for connection to external preamplifier circuitry.

The lead cable region 335 is formed from the union of the separate lead sections 336 and 337 of the sensor heads 353 and 354 and a common shared lead cable region 338 for attachment to the connector region 340. The constructional architecture of the separate lead sections 336 and 337 of the cable 335 are identical to that of the lead cable regions 35 and 135 as described in sensor embodiments 11 and 111 respectively, and allow each of the sensor heads 353 and 354 to be independently positioned and an aligned with the muscle fibers 364 and 365 of each respective muscle bundle 366 and 367.

The constructional architecture of the independent sensor heads 353 and 354 of sensor embodiment 211 is substantially similar to that of the sensor head regions 30 and 130 as described in sensor embodiments 11 and 111 respectively. The sensor heads can be configured to form a sensor array consisting of: a) multiple iterations of the single differential sensor configuration as shown in FIG. 12, b) multiple iterations of the double differential sensor configuration as shown in FIG. 18, or c) a combination of both single and double differential sensor configurations.

Obviously, many modifications and variations of the present invention are possible in light of the above teachings. It is to be understood, therefore, that the invention can be practiced otherwise than as specifically described.

What is claimed is:

1. A biomedical sensor that provides an electrode to body interface, comprising:
   a plurality of individual electrically conductive, adhesive, cross-linked hydrophilic polymer gel substrate layers which form a plurality of signal detection electrode contacts and an elongated electrically conductive polymer reference electrode contact;
   a plurality of insulated conductor leads electrically connected to the electrode contacts and extending away from the electrode contacts, the leads being embedded and fully enveloped lengthwise within the elongated electrically conductive hydrophilic polymer reference electrode contact to form a lead cable shielding the sensor and leads from external electrical fields and suppressing movement artifact while providing a conformable, contoured attachment of the sensor and lead cable to underlying skin of the body; and
   a conformable framework mechanically supporting and electrostatically shielding the insulated conductor leads and electrode contacts.

2. A biomedical sensor as in claim 1 wherein each electrically conductive, adhesive, cross-linked hydrophilic polymer gel signal detection electrode contact is disposed on and retained by a body-directed insulating substrate layer of a double-sided adhesive sheet.

3. A biomedical sensor as in claim 2 wherein an electrically conductive electro-static shield substrate layer is adhered to and retained by an upper surface of the insulating substrate of the double-sided adhesive sheet, and contoured to match a profile of an underlying substrate to make mechanical and electrical contact with the electrically conductive, adhesive, cross-linked hydrophilic polymer gel reference contact.

4. A biomedical sensor as in claim 3 wherein the electro-static shield substrate layer is formed from an electrically conductive metallic sheet.

5. A biomedical sensor as in claim 3 wherein the electro-static shield substrate layer is formed from an electrically conductive plastic sheet.

6. A biomedical sensor as in claim 3 wherein the electro-static shield substrate layer is formed from an electrically conductive hydrophilic polymer gel.

7. A biomedical sensor as in claim 3 wherein a malleable stabilizing substrate is adhered to and retained by an upper surface of the electrically conductive shield substrate and contoured to match the profile of the underlying substrate layer thereby supporting the underlying electrode contacts.

8. A biomedical sensor as in claim 1 wherein an insulated, conformable top covering layer is adhered to top surfaces of the sensor.

9. A biomedical sensor as in claim 8 wherein the conformable top covering layer is cosmetically textured and colored to more closely match color and texture of the underlying skin.

10. A biomedical sensor as in claim 1 wherein the electrically conductive, adhesive, cross-linked hydrophilic polymer gel substrate layers are configured as a plurality of signal detection contacts and one reference contact, each having a respective length of insulated conductor lead which mechanically and electrically terminates in the contacts of a connector block.

11. A biomedical sensor as in claim 10 wherein the insulated conductor leads for each of the signal and reference contacts are formed with one or more strands of electrically conductive wire.

12. A biomedical sensor as in claim 10 wherein the insulated conductor leads for each of the signal and reference contacts are formed from electrically conductive printed circuit traces on a conformable insulating substrate.

13. A biomedical sensor as in claim 12 wherein the terminating printed circuit traces from each of the conductor leads are shaped and retained on a rigid substrate to form connector contacts.

14. A biomedical sensor as in claim 10 wherein a region of the respective insulated conductor leads for each of the signal and reference contacts is un-insulated and embedded within an upper surface of the electrically conductive, adhesive, cross-linked hydrophilic polymer gel to make an electrical contact.

15. A biomedical sensor as in claim 10 wherein each of the electrically conductive areas of the signal contacts is formed from a sheet of electrically conductive, adhesive, cross-linked hydrophilic polymer gel in the shape of a rectangle with a bottom surface aligned in parallel and coplanar with a body-directed insulating adhesive substrate.

16. A biomedical sensor as in claim 10 wherein each of the electrically conductive areas of the signal contacts is formed from a sheet of electrically conductive, adhesive, cross-linked hydrophilic polymer gel in a shape of a disc with a bottom surface aligned in parallel and coplanar with a body-directed insulating adhesive substrate.

17. A biomedical sensor as in claim 10 wherein the reference contact is formed from a sheet of electrically conductive, adhesive, cross-linked hydrophilic polymer gel in the shape of an elongated rectangular strip aligned linearly and in a plane of the signal contacts and extending away from the signal contacts so as to form a separate length of conducting reference electrode surface.

18. A biomedical sensor as in claim 10 wherein the electrically conductive contact areas form a linear array of two symmetrically spaced signal contacts that detect signals using a differential recording technique.

19. A biomedical sensor as in claim 18 wherein the electrically conductive signal areas are arranged to form a sensor array having multiple linear array elements that detect signals from multiple detection sites using one or more single differential sensor configurations and double differential sensor configurations.

20. A biomedical sensor as in claim 10 wherein the electrically conductive signal areas form a linear array of three symmetrically spaced signal contacts that reduce crosstalk signals using a double differential recording technique.

21. A biomedical sensor as in claim 20 wherein the electrically conductive signal areas are arranged to form a sensor array having multiple linear array elements that detect signals from multiple detection sites using one or more single differential sensor configurations and double differential sensor configurations.

22. A biomedical sensor as in claim 1 wherein the sensor is single use and disposable.

* * * * *